United States Patent [19]

Rösch et al.

[11] Patent Number: 5,702,777
[45] Date of Patent: Dec. 30, 1997

[54] SILANE COUPLERS CONTAINING CYCLIC STRUCTURAL ELEMENTS AS ALIGNMENT FILMS

[76] Inventors: Norbert Rösch, Geisenheimer Strasse 95, D-60529 Frankfurt/Main; Peter Wegener, Am Eichkopf 4, D-61462 Königstein, both of Germany

[21] Appl. No.: 650,591

[22] Filed: May 20, 1996

Related U.S. Application Data

[63] Continuation of Ser. No. 201,557, Feb. 24, 1994, abandoned.

[30] Foreign Application Priority Data

Feb. 26, 1993 [DE] Germany ............ 43 05 970.8

[51] Int. Cl.$^6$ ............................................ G02F 1/1337
[52] U.S. Cl. .................. 428/1; 428/447; 556/465; 556/423; 556/489; 556/445; 556/413
[58] Field of Search ............ 428/1, 447; 556/465, 556/423, 489, 413, 445

[56] References Cited

FOREIGN PATENT DOCUMENTS

| 2 040 876 | 4/1991 | Canada. |
|---|---|---|
| 2040876 | 4/1991 | Canada. |
| 0386782 | 9/1990 | European Pat. Off.. |
| 0453966 | 10/1991 | European Pat. Off.. |
| 0528415 | 2/1993 | European Pat. Off.. |
| 41 27 287 | 2/1993 | Germany. |

OTHER PUBLICATIONS

Sagiv et al., Adsorbed Monolayers. Molecular Organization and Electrical Properties, p. 883, Jul. 1978.
Ogawa et al., Languir 1991, Studies of Molecular Alignments of Monolayers Deposited by a Chemical Absorption Technique, pp. 1473–1477.
Derwent Abstract No. 008814543.
Hawley's Condensed Chemical Dictionary, p. 216, 1993.
Hackh's Chemical Dictionary, 1984.
Organometallics, vol. 112, 1990, p. 815, 112: 77312s.
Chemical Abstracts, vol. 100, 1984, p. 6, 100: 121709e.
German Abstract No. DE 4127287–A1.
J. Org. Chem. 1988, 53, pp. 3190–3195, Bradshaw et al. "Synthesis of (Allyloxy)methyl–Substituted Diaza–18–crown–6 Compounds for Attachment to Silica Gel".
WO93/04142 PCT/EP92/01895 relates to EP 0,528,415.

*Primary Examiner*—Margaret W. Glass

[57] ABSTRACT

An alignment film for liquid crystals comprising a quasi-monomolecular layer of compounds of the formula II $$C_y - S_p - A_n \quad (II)$$

in which $C_y$ is a mediocyclic or macrocyclic carbon ring having 8 or more ring members, it also being possible for this ring to contain fused benzene rings and —O—, —N—, —S—, —Si— and —B— as heteroatoms;

$S_p$ is an alkyl group having from 1 to 20 carbon atoms, in which one or more non-adjacent —CH$_2$—groups may be replaced by —O—, —S—, —CO—, —O—CO—, —NH—CO—, —O—COO—, —NH—CO—NH—, —NH—CO—O—, —SO$_2$—, —Si(CH$_3$)$_2$—, —CH=CH— or —C≡C—;

$A_n$ is SiX$^1$X$^2$X$^3$, where X$^1$ is a single bond, and X$^2$ and X$^3$, independently of one another, are a single bond or an alkyl or alkoxy group, where the compound of the formula (II) is bonded to an oxidic layer via the single bond(s) of the group $A_n$.

The alignment films according to the invention are highly suitable for the alignment of liquid crystals, in particular ferroelectric liquid crystals. The low thickness of the alignment film prevents dielectric losses in the display. The occurrence of ghost images is substantially suppressed.

10 Claims, No Drawings

SILANE COUPLERS CONTAINING CYCLIC STRUCTURAL ELEMENTS AS ALIGNMENT FILMS

This application is a continuation of application Ser. No. 08/201,557, filed Feb. 24, 1994, now abandoned.

BACKGROUND OF THE INVENTION

Switching and display devices containing ferroelectric liquid-crystal mixtures (FLC displays) are disclosed, for example, in EP-B 0 032 362 (=U.S. Pat. No. 4,367,924). Liquid-crystal displays are devices which, for example due to electric switching, can change their optical transmission properties in such a way that incident (and possibly reflected) light is modulated in intensity. Examples are the known watch and calculator displays or liquid-crystal displays in the OA (office automation) or TV sectors (see also Liquid Crystal Device Handbook, Nikkan Kogyo Shimbun, Tokyo, 1989; ISBN 4-526-02590-9C 3054 and the papers cited therein).

These FLC displays are built up in such a way that a liquid-crystal layer is enclosed on both sides by layers which are usually, in this sequence starting from the FLC layer, at least one alignment layer, electrodes and a limiting plate (for example made of glass). Additionally, they contain one polarizer if they are operated in "guest-host" or reflective mode or two polarizers if the mode used is transmissive birefringence. Switching and display elements may also contain further ancillary layers, such as diffusion barrier or insulation layers.

The alignment layers, which comprise an organic (for example polyimide, polyamide or polyvinyl alcohol) or inorganic (for example SiO) material, together with a spacing between the limiting plates which is selected to be sufficiently small, bring the FLC molecules of the mixture into a configuration in which the molecules lie with their long axes parallel and the smectic planes are arranged perpendicular or inclined with respect to the alignment layer. In this arrangement, the molecules, as is known, have two equivalent alignments, between which they can be switched by applying a pulsed electric field, i.e. FLC displays are capable of bistable switching. The response times are inversely proportional to the spontaneous polarization of the FLC mixture and are in the region of microseconds.

In addition to the abovementioned alignment layers built up from organic polymers, alignment layers can also comprise amphiphilic substances applied as a monomolecular, aligned layer by the Langmuir-Blodgett technique (see, for example, K. Hiltrop, H. Stegemeyer, Bet. Bunsenges. Phys. Chem. 82, 883 (1978)). Another method for building up a quasi-monomolecular alignment layer is the silanization of the FLC display, i.e. of the glass and the electrode applied. This method, which has long been used in various areas, is significantly simpler to carry out than the Langmuir technique and comprises reacting and firmly bonding alkylsiloxanes, for example R—SiX$_3$ or R$_2$SiX$_2$, where X=O-alkyl or halogen, with the glass surface with elimination of HX and formation of an Si—O—Si bond. The process is described, for example, by K. Ogawa, M. Mino, K. Makajima, Y. Azuma, T. Okumura in Langmuir 1991, 1473–1477, and EP-A-0 386 782. However, the contrast and brightness values achieved using this method are not adequate for all applications.

A particularly favorable method of improving the contrast and histability of the switching states has proven to be modification of polymeric alignment layers with substances containing cyclic structural elements, for example with crown ethers, azacrowns and carbocycles (see, for example, WO-A 92/13290).

Such compounds, which are chemically fixed to the polymer surface, generally comprise cyclic structural elements, a spacer group and a reactive group, which enables binding to the surface. The reactive groups are, for example, halogens or hydroxyl groups. EP-A-0 453 966 also describes two compounds containing silicon-containing reactive groups. According to the prior art, the compounds containing cyclic structural elements are applied in a separate step to an organic polymer alignment layer applied in advance and are subsequently fixed by heating.

This double application means more work, which is particularly disadvantageous for industrial mass production. In addition, the multiple application increases the thickness of the alignment layer. However, relatively thick layers can under certain circumstances result in dielectric losses in the alignment layer and thus in the increased occurrence of ghost images.

The object was therefore to develop alignment layers which enable very good contrast and brightness values at the same time as a very small layer thickness.

SUMMARY OF THE INVENTION

It has now been found that certain silicon-containing compounds which contain cyclic structural elements are highly suitable as alignment films for liquid crystals, in particular ferroelectric liquid crystals.

The invention relates to a silicon-containing coupling reagent of the formula (I)

$$C_y—S_p—R_g \qquad (I)$$

in which $C_y$ is a mediocyclic or macrocyclic carbon ring having 8 or more ring members, it also being possible for this ring to contain fused benzene rings and —O—, —N—, —S—, —Si— and —B— as heteroatoms;

$S_p$ is an alkyl group having from 1 to 20 carbon atoms, in which one or more non-adjacent —CH$_2$— groups may be replaced by —O—, —S—, —CO—, —O—CO—, —NH—CO—, —O—COO—, —NH—CO—NH—, —NH—CO—O—, —SO$_2$—, —Si(CH$_3$)$_2$—, —CH=CH— or —C≡C—;

$R_G$ is —SiX$^1$X$^2$X$^3$, where

X$^1$ is C$_1$-C$_{10}$-alkoxy, F, Cl or Br, and

X$^2$ and X$^3$, independently of one another, are C$_1$-C$_{10}$-alkyl, C$_1$-C$_{10}$-alkoxy, Cl or Br, with the exception of the compounds

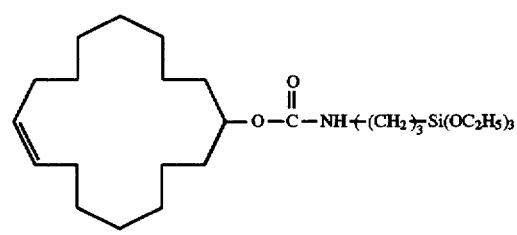

and

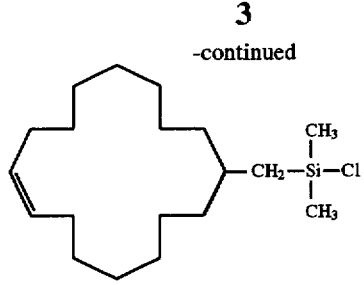

The invention furthermore relates to an alignment film for liquid crystals, comprising one or more compounds of the formula II $$C_y-S_p-A_n \quad (II)$$

in which $C_y$ and $S_p$ are as defined in the formula I, and $A_n$ is $SiX^1X^2X^3$, where $X^1$ is a single bond, and $X^2$ and $X^3$, independently of one another, are a single bond or an alkyl or alkoxy group, where the compound(s) of the formula (II) are bonded to an oxidic substrate via the single bond(s) of group $A_n$.

DESCRIPTION OF THE PREFERRED EMBODIMENTS

The films according to the invention produced from the silicon-containing coupling reagents according to the invention are highly suitable for the alignment of liquid crystals, in particular ferroelectric liquid crystals. The low thickness of the alignment film prevents dielectric losses in the display. The occurrence of ghost images is suppressed.

Preferred compounds of the formula I are those in which $C_y$ is a carbocyclic ring having 12 to 30, in particular 15 to 27, ring members, where from one to four benzene rings may be fused on and one or more oxygen and/or nitrogen atoms may be present.

Particularly suitable carbocycles are rings having 16, 17 or 24 ring members, for example muscone derivatives, cyclohexanedecanone derivatives, zibetone derivatives or derivatives of cyclotetracosadiene and -triene, obtainable by metathesis reaction, for example from cyclooctadiene, cyclododecadiene or by ring expansion reaction of cyclohexadecenone. Heterocyclic compounds which are particularly advantageous are derivatives of crown ethers and derivatized aza- and diazacrown ethers, for example functionalized alkoxy-15-crown-6, alkoxy-18-crown-6, 1-aza-15-crown-5, 1-aza-18-crown-6, and 1,10-diaza-18-crown-6.

Examples of preferred ring structures are:

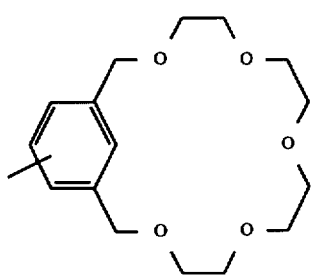

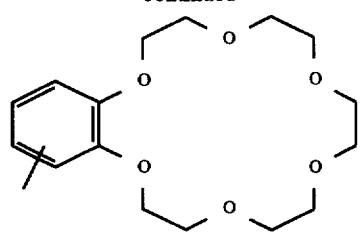

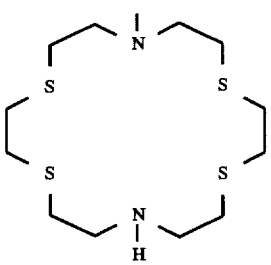

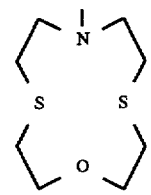

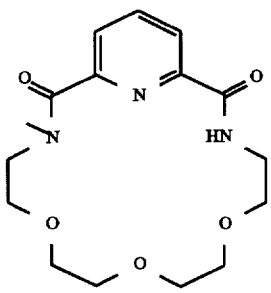

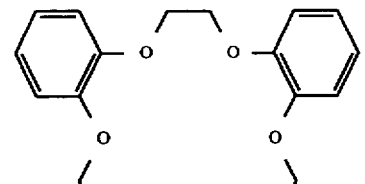

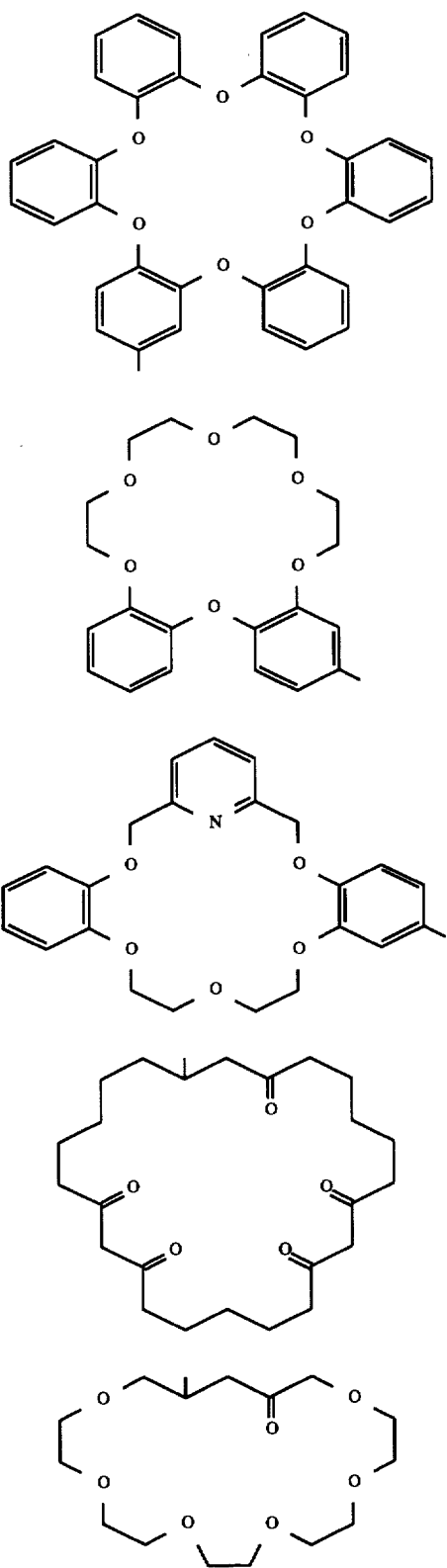
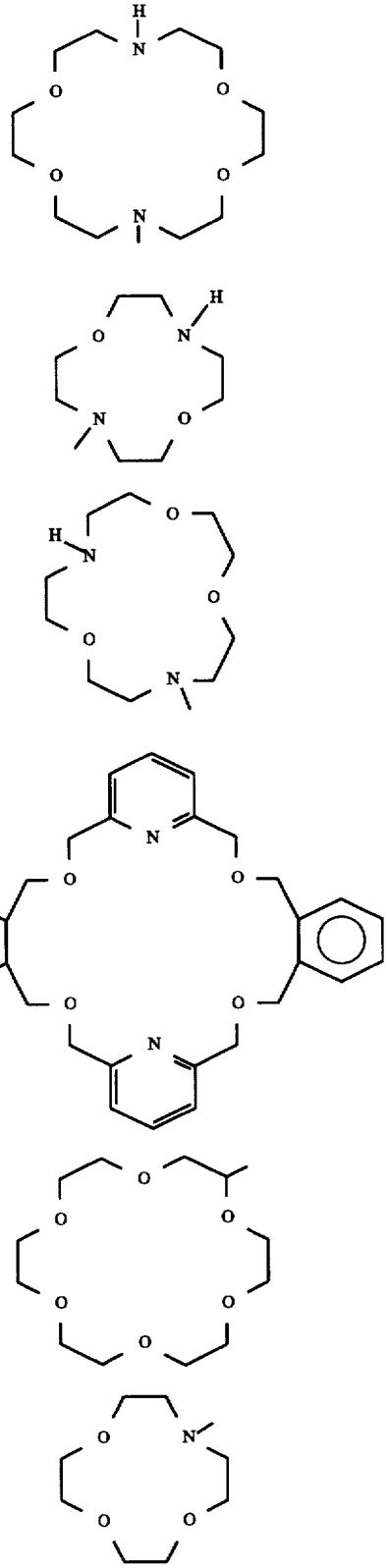

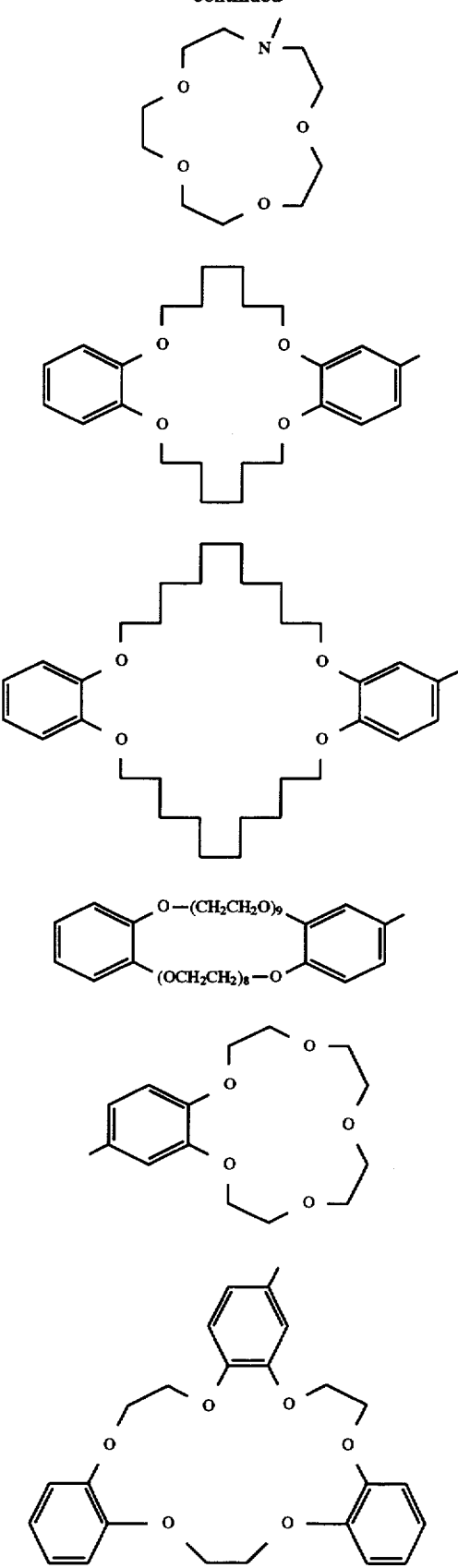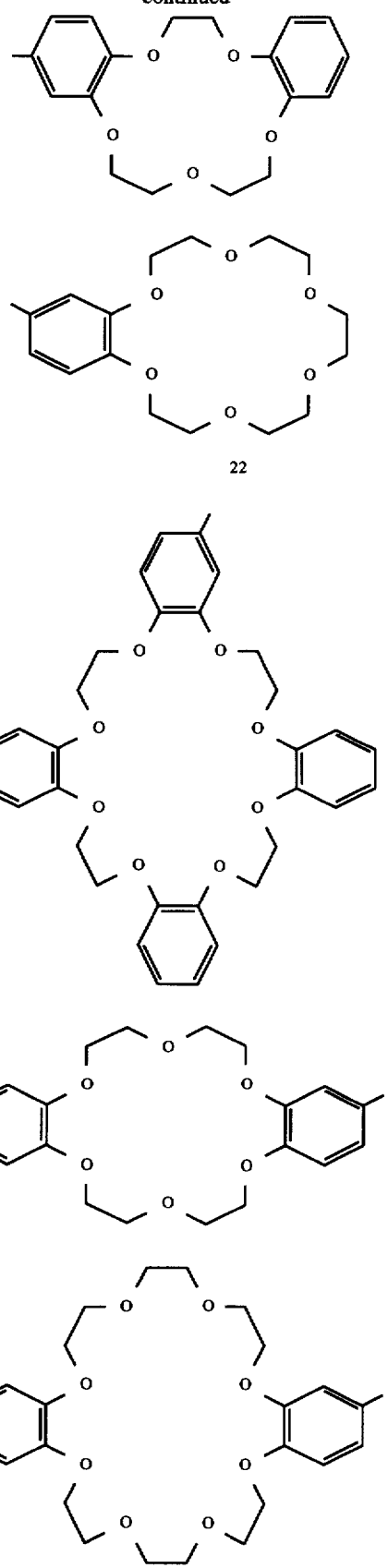

-continued

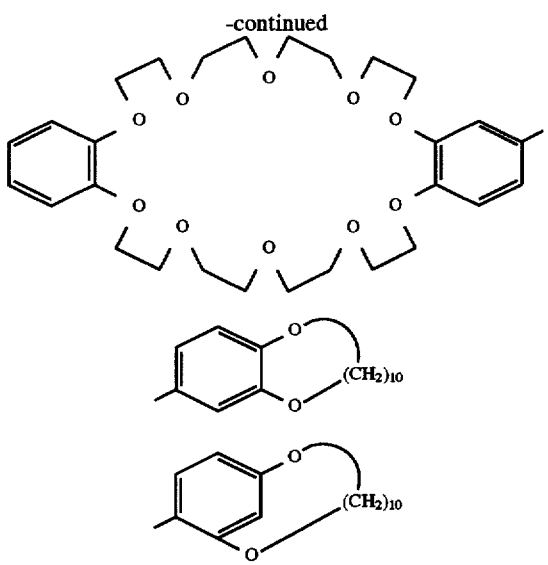

The spacer group, $S_p$, is preferably an alkylene group having 1 to 16 carbon atoms, where from one to three, preferably one or two, non-adjacent —$CH_2$— groups may be replaced by —O—, —CO—, —O—CO—, —NH—CO—, —O—CO—O—, —CH=CH—, —NH—CO—O— or —NH—CO—NH—.

Particularly preferred spacers are those having 3 to 12 chain members, where one or two —$CH_2$— groups may be replaced by —O—, —CO—, —NH—CO—, —NH—CO—NH— or —NH—CO—O—.

Examples of suitable spacers are derivatized 1,2-, 1,3-, 1,4-, 1,6- and 1,8-alkanediols, such as derivatives of glycol, propanediol, butanediol, 2-butanediol, 1,6-hexanediol and 1,8-octanediol, and furthermore 6-hydroxycaproic acid derivatives, 6-aminocaproic acid derivatives, 1,9-nonanedicarboxylic acid or, as the basis for spacers, allylacetic acid. Di- and triethylene glycols are also suitable as spacers.

The reactive silicon-containing group $R_G$ is preferably —$Si(CH_3)_2Cl$; —$Si(O-alkyl)_3$, in particular —$Si(OC_2H_5)_3$ and —$Si(OCH_3)_3$; —$Si(CH_3)$ (O-alkyl)$_2$, in particular —Si(CH$_3$) (OC$_2$H$_5$)$_2$ and —Si(CH$_3$) (OCH$_3$)$_2$; and —Si(CH$_3$)$_2$—O-alkyl, in particular —Si(CH$_3$)$_2$(OC$_2$H$_5$) and —Si(CH$_3$)$_2$(OCH$_3$).

The compounds according to the invention are synthesized by known methods customary to a person skilled in the art. For example, it is possible to synthesize macrocycles, to which spacer and silyl groups can be attached by suitable linking reactions.

The synthesis of macrocycles which can be converted into the corresponding coupling reagents according to the invention is described, for example, in WO-A 90/02018, EP-A-0 451 822 and EP-A-0 453 966, and the references cited therein.

Many such compounds, for example azacrown ethers, such as 1-aza-12-crown-4, 1-aza-15-crown-5 and 1-aza-18-crown-6, are commercially available, for example from Fluka and Buchs.

The macrocycle is likewise linked to the spacer by known, customary methods. For example, azacrown ethers can be reacted with acid chlorides to give the corresponding amides or react with isocyanate to give the corresponding urea derivatives. Macrocycles carrying OH groups react with isocyanates to give the corresponding urethanes or can be converted into ethers using suitable reagents.

Macrocycles containing keto groups can form a C—C single bond with the spacer group, for example via a Wittig reaction followed by hydrogenation.

The reactive silicon-containing group can be introduced, for example, by hydrosilylation of a double bond present in the spacer group.

Reactive organosilyl compounds which can be linked to the spacer fragment can be prepared by methods known per se (for example C. Eaborn et al., in Organometallic Compounds of the Group IV Elements, Vol. 1, Part 1, Dekker New York, 1968; E. Lukevics et al., in J. Organomet. Chem. Libr. 5, 1 (1977) or R. Heumer et al., in Houben-Weyl Methoden der org. Chemie [Methods of Organic Chemistry], E 18/2, p. 685 ff., Thieme-Verlag, Stuttgart-New York, 1986).

The linking is then carried out, for example, by hydrosilylation of a double bond present in the spacer group.

Thus, unsaturated compounds can be reacted with dialkylchlorosilanes $HSiX^2X^3Cl$ in the presence of a noble metal catalyst (for example $H_2PtCl_6$ in isopropanol) and, if desired, in the presence of an inert organic solvent at temperatures between 0° and 150° C., the silane advantageously being employed in excess.

Another way of linking the silicon functionality to the spacer group comprises reacting silicon-containing cyanides, such as 3-cyanopropyldimethylchlorosilane, 3-cyanopropyltriethoxysilane and 3-cyanopropyltrichlorosilane, which are commercially available, with spacer fragments having an NH or OH function, forming spacer groups containing urethane or urea structures.

In order to produce the alignment film according to the invention, the compounds according to the invention are coupled to oxidic substrates. For example, they can be applied directly to the glass substrate or to the electrode. The electrode preferably comprises indium-tin oxide (ITO). However, it is also possible to apply the alignment film according to the invention to an insulation layer, for example of $SiO_2$ or $Ta_2O_5$, on top of the electrode.

The compound according to the invention is applied, for example, by dip coating or spin coating, where the compound of the formula I according to the invention is dissolved in a suitable, preferably polar, aprotic solvent, such as 1-methoxy-2-propanol or dioxane. The content of the compound according to the invention in the solution is from 0.001 to 0.1% by weight, preferably from 0.005 to 0.05% by weight, based on the entire solution.

The fixing is generally carried out thermally by heating at from 80 to 150° C., preferably at from 100 to 145° C., for 10–30 minutes. Fixing by microwaves or ultrasound is also possible. The substrates are then rubbed in a conventional manner and subsequently assembled to form the display.

The invention also relates to a process for the production of an alignment film for liquid crystals, in which a compound of the formula I, dissolved in a polar aprotic solvent, is applied to an oxidic substrate by spin coating, after which thermal fixing at from 80 to 150° C. and aftertreatment by rubbing are carried out.

The alignment film can also be built up using mixtures of various ring sizes or analogous compounds containing spacers of different lengths. Preferably such a mixture comprises 1 to 5 compounds of the formula (I). It is also possible to use diazocrowns containing a doubled spacer-silocane function.

A similar effect as obtained using the compounds of the formula I described above can also be achieved using chain-form molecules containing reactive, silicon-containing groups at both ends. After fixing to an oxidic substrate, these compounds form a loop together with the substrate.

Examples of such chain-form molecules are products of the reaction of polyethers containing 2 terminal amino groups (for example Jeffamine®-400, commercial product from Texaco) with 2 mol of isocyanatosiloxanes, for example

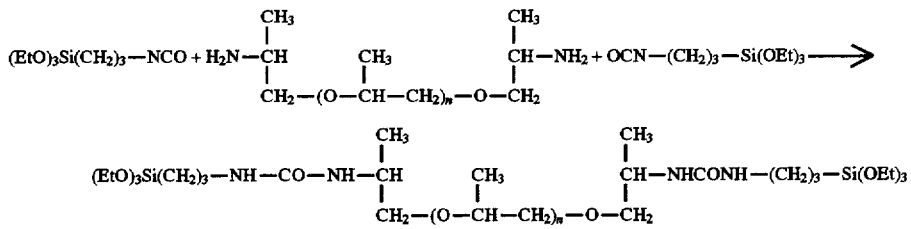

where n=1 to 10.

On application to, for example, a glass surface, the two anchor groups, SiOEt$_3$, close a loop together with this surface.

The invention is described in greater detail by means of the examples.

EXAMPLE 1

N-(aza-18-crown-6)-11-(triethoxysilyl) undecylcarboxamide

A solution of 9 g of 1-aza-18-crown-6 and 8 ml of triethylamine in 30 ml of dichloromethane is added dropwise to 4 ml of 10-undecenylcarbonyl chloride in 70 ml of dichloromethane. The mixture is initially cooled by means of ice water, then stirred at room temperature for 6 hours. The precipitate of triethylammonium hydrochloride is filtered off with suction via a frit, and the filtrate is evaporated.

The residue, 14.7 g, is purified by column chromatography on silica gel using dichloromethane:methanol=19:1 as eluent, giving 8.5 g of N-(aza-18-crown-6)-10-undecenylcarboxamide, 98% pure according to GC.

3.12 g of this are dissolved in 40 ml of oxygen-free toluene in a dry flask under a blanket of argon, and 1.5 ml of triethoxy-H-silane and 0.1 ml of tetramethyldivinylsiloxane/platinum as catalyst are added, and the mixture is refluxed for 72 hours under Ar. The dark solution is then freed from solvent and chromatographed over silica gel using dichloromethane:isopropanol=19:1 as eluent, giving 1.4 g of N-(aza-18-crown-6)-11-triethoxysilyl-undecylcarboxamide, 94.7% pure according to GC. IR(KCl) C=O up to 1700 cm$^{-1}$, NH (broad) up to 3300 cm$^{-1}$

| NMR: | quartet | 3.78 ppm, area 6 | |
|---|---|---|---|
| | triplet | 1.15 ppm, area 9 | —OC$_2$H$_5$ |
| | multiplet | 3.70 ppm, area 24 | azacrown |
| | triplet | 2.25 ppm, area 2 | |
| | multiplet | 1.30 ppm, area 16 | |

EXAMPLE 2

(Triethoxysilylpropyl)aza-18-crown-6-urea

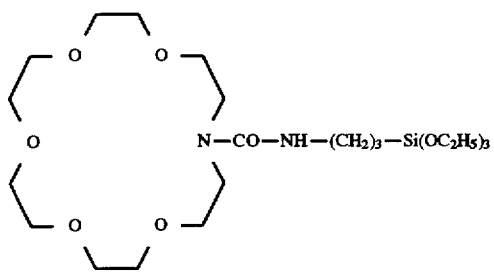

1 ml of isocyanatopropyltriethoxysilane is added to 1 g of 1-aza-18-crown-6, dissolved in 10 ml of dioxane, and the mixture is warmed at 100° for 3 hours.

After 3 hours, the isocyanate band at 1250 cm$^{-1}$ in the IR has disappeared, and a urea-C=O band appears at 1670 cm$^{-1}$. After the solvent has been removed by distillation, the product is purified by chromatography on SiO$_2$ using CH$_2$Cl$_2$:ethanol=9:1 as eluent, giving 1.1 g of substance with a purity of 94% (according to GC).

The NMR spectrum shows:

| triplet | 6.0 ppm, area 1, NH | |
|---|---|---|
| quartet | 3.8 ppm, area 6 | —O—CH$_2$—CH$_3$ |
| triplet | 1.15 ppm, area 9 | —O—CH$_2$—CH$_3$ |
| multiplet | 3.7 ppm, area 24 | azacrown |
| quartet | 3.05 ppm, area 2 | N—CH$_2$— |
| multiplet | 1.5 ppm, area 2 | propyl radical |
| multiplet | 0.6 ppm, area 2 | Si—CH$_2$ |

Starting from 1-aza-15-crown-5, the same process gives a corresponding compound containing aza-15-crown-5.

EXAMPLE 3

N,N'-bis(1,10-diaza-18-crown-6) triethoxysilylpropylurea 0.5 g of 1,10-diaza-18-crown-6 is dissolved in 10 ml of THF, 1.0 ml of isocyanatopropyltrimethoxysilane is added, and the mixture is refluxed for 8 hours. The THF is then removed by distillation, and the residue is chromatographed over SiO$_2$ using CH$_2$Cl$_2$:ethanol=9:1, giving a fraction of 0.8 g of a liquid which comprises 90% (according to GC) of the desired di-adduct and 10% of the mono-adduct. Further chromatography allows the desired di-adduct to be obtained in a purity of >95%.

| NMR: | triplet | 5.9 ppm, area 1 | NH |
| --- | --- | --- | --- |
| | quartet | 3.8 ppm, area 6 | —OC$_2$H$_5$ |
| | triplet | 1.2 ppm, area 9 | —OC$_2$H$_5$ |
| | multiplet | 3.7 ppm, area 12 | azacrown |
| | quartet | 3.05 ppm, area 2 | propyl radical |
| | multiplet | 1.5 ppm, area 2 | propyl radical |
| | multiplet | 0.6 ppm, area 2 | propyl radical |

EXAMPLE 4

8-Cyclohexadecenyl 3-triethoxysilylpropylcarbamate 1 ml of 3-isocyanatopropyltriethoxysilane and 50 mg of triethylamine are added to 0.9 g of 8-cyclohexadecen-1-ol, prepared by reduction of 8-cyclohexadecen-1-one using NaBH$_4$ in ethanol, and the mixture is kept at 80° C. for 24 hours. Low-boiling components are removed at 90° C./0.1 mbar. The residue solidifies on cooling to form a wax and shows only traces of an isocyanate band in the IR spectrum, but instead a strong band (1700 cm$^{-1}$) of the

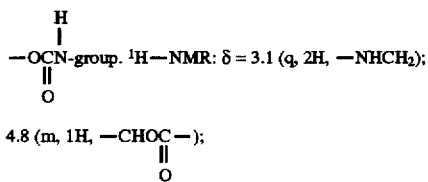

5.2(m, 2H, —CH=CH—); 0.6 (m, —CH$_2$Si).

According to GLC, the compound has an (extrapolated) boiling point of 427° C.

EXAMPLE 5

Chlorodimethylsilylmethylcyclohexadec-8-ene 10.7 g of triphenylmethylphosphonium bromide are added at room temperature to a mixture of 20 ml of n-butyllithium (1.55 molar in hexane) and 60ml of diethyl ether. After the mixture has been held at room temperature for 4 hours, 7.3 g of 8-cyclohexadecen-1-one are added dropwise, and the mixture is refluxed for 18 hours. After filtration, the solvent is removed by distillation, the residue is purified by chromatography (SiO$_2$, hexane/ethyl acetate 95:5), giving 2.5 g of 1-methylene-8-cyclohexadecene, identified by a $^1$H-NMR spectrum:

δ=5.2 (t, —CH=CH—); δ=4.75 (s, C=CH$_2$).

2.5 g of the above compound are warmed at 60° C. for 24 hours with 2.0 ml of dimethylchlorosilane and 0.5 ml of platinum/divinyltetramethyldisiloxane complex (10% in xylene) in a pressure vessel. Distillation gives 3.1 g of product of boiling point 105–110° C./0.01mbar; $^1$H-NMR: δ=5.2 (m, 2H, —CH=CH—); 0.85 (m, 2H, —CH$_2$Si); 0.3 (s, 6H, —CH$_3$).

USE EXAMPLES

Construction of test cells

In order to demonstrate the advantageous properties of the alignment films according to the invention, test cells are produced, filled with a ferroelectric liquid-crystal mixture and subsequently tested.

To this end, glass plates coated with indium-tin oxide (ITO) and structured are cleaned at 60° C. in an ultrasound bath first in an aqueous surfactant solution and subsequently twice in water which has been purified via a Millipore filter unit. After the glass substrates have been dried by means of hot air, they are coated with the corresponding compounds according to the invention dissolved in 1-methoxy-2-propanol (0.01% strength by weight). The coating is carried out by means of a spin coater, but can also be carried out using other methods, for example printing, spraying or dip coating. The solutions are dripped onto the glass substrate, pre-spun for 5 seconds at 500 rpm and then subjected to the principal spinning for 30 seconds at 4000 rpm. The wet film is dried at 150° C. for 30 minutes. The dried film is subsequently rinsed for 5 minutes with isopropyl alcohol in an ultrasound bath and rubbed with a velvet-like material, and the substrates are bonded together to form the cells according to the invention.

The alignment films used are the following silanes, applied in the manner described above:

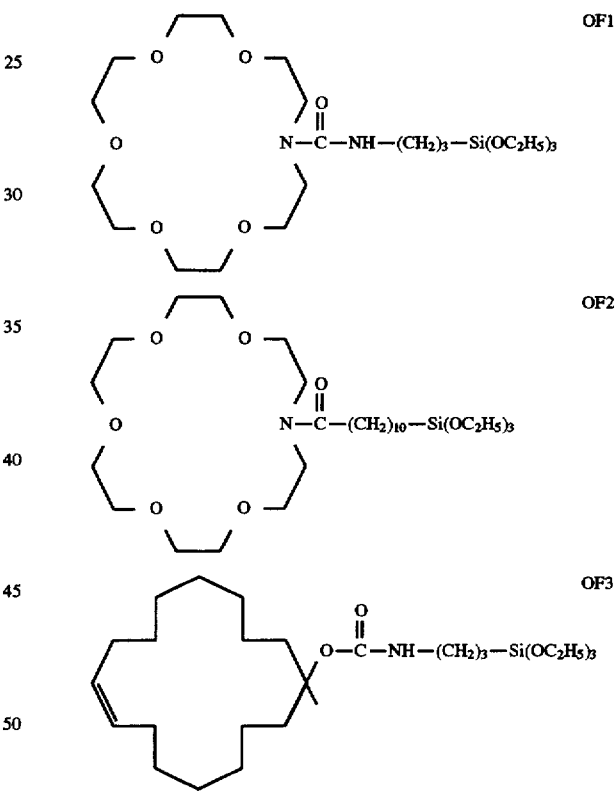

EXAMPLES

Measurement examples (characterization of the alignment films according to the invention)

The alignment films according to the invention are characterized using ferroelectric liquid-crystal mixtures. Assessment is made of the alignment of the liquid crystal in the test cell containing the alignment film according to the invention; the switching behavior of the liquid crystal on application of short addressing pulses simulating operation of a matrix display, and the optical contrast, which is the ratio between the transmissions in the bright and dark switching states.

The alignment films according to the invention are used both in the chevron structure described at the outset and in the bookshelf or quasi-bookshelf structure. The bookshelf structure is induced starting from the chevron structure by applying a rectangular voltage of about 10 Hz at an amplitude of about 10–15 V/µm. The cells are positioned in the ray path of a polarizing microscope to which a photodiode is additionally attached. The photodiode is connected to a storage oscilloscope and enables recording of the optical transmission of the liquid-crystal cell.

A freely programmable function generator with downstream voltage amplifier supplies the test cell with the switching pulses necessary for switching. Various pulse shapes can be defined for the function generator via a computer interface. One of the pulse shapes used simulates operation of the 1-pixel test cells employed in a matrix display. The ratio between line and voltage (data pulses) is an important parameter here, which is defined as the bias ratio. This ratio should be as large as possible, since a correspondingly high contrast only becomes possible at a low data-pulse amplitude.

As a further important parameter, the effective tilt angle is used to characterize the alignment films. For the bookshelf geometry of the smectic layers, twice the tilt angle is identical to the switching angle. The effective tilt angle in the chevron structure is less than the molecular tilt angle (inclination of the molecules with respect to the layer normals) as a consequence of the angled layer structure.

So-called twist or bend states result in a further reduction in the effective tilt angle. The bluish color observed here in the dark switching state and the low transmission in the bright state result in an extremely low contrast.

The effective tilt angle in the bookshelf structure is significantly greater, and the bright state is thus distinguished by greater brightness. However, the occurrence of twist states can again result in a considerable drop in contrast here. The alignment films according to the invention can substantially suppress the formation of twist states.

The FLC mixture M1 employed has the following composition (in mol %):

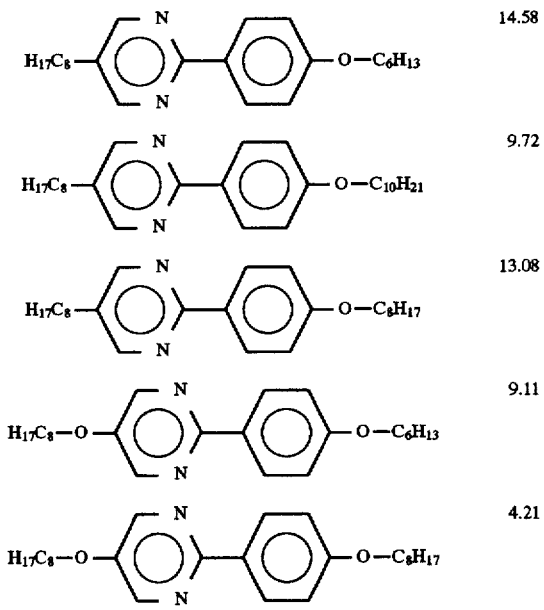

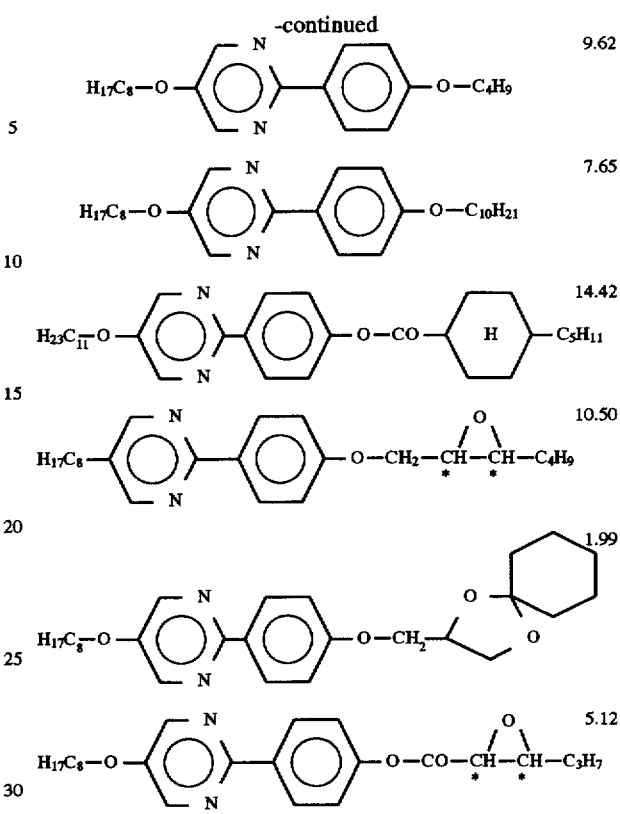

and has the phase sequence S*$_c$ 65 S$_A$ 73 N* 86 I and a spontaneous polarization of 38 nC.cm$^{-2}$ at a temperature of 25° C.

The effective tilt angle of the liquid crystal is assessed in the chevron structure which is formed immediately after filling of the cells. By contrast, the multiplex and switching properties are measured in the bookshelf or quasi-bookshelf structure, which is obtained from the chevron structure by applying a rectangular voltage (10–15 V/µm at 10 Hz, 30 s).

Test cells containing the alignment films according to the invention are filled with the ferroelectric liquid-crystal mixture M1. The reference example used is a cell containing a rubbed ITO electrode as the alignment layer. The results are shown in Table 1.

TABLE 1

| Characterization of the alignment films according to the invention (AF) | | | | |
|---|---|---|---|---|
|  | AF1 | AF2 | AF3 | Reference (rubbed ITO electrode) |
| Effective tilt angle | 10° | 10° | 10° | 8° |
| Twist states | no | no | no | yes/in some cases |
| Maximum bias under multiplex conditions | ~5 | ~4 | ~5 | multiplexes not possible |

We claim:
1. An alignment film for liquid crystals, consisting of one or more compounds of the formula II

$$C_y\text{—}S_p\text{—}A_n \qquad \text{(II)}$$

in which $C_y$ is a mediocyclic or macrocyclic carbon ring having 8 or more ring atoms;

$S_p$ is an alkyl group having from 1 to 20 carbon atoms, in which one or more non-adjacent —$CH_2$—groups may be replaced by —O—, —S—, —CO—, —O—CO—, —NH—CO—, —O—COO—, —NH—CO—NH—, —NH—CO—O—, —$SO_2$—, —$Si(CH_3)_2$—, —CH=CH— or —C≡C—;

$A_n$ is $SiX^1X^2X^3$, wherein $X^1$ is a single bond, and $X^2$ and $X^3$, independently of one another, are a single bond or a $C_1$–$C_{10}$-alkyl or $C_1$–$C_{10}$-alkoxy group, where the compound(s) of the formula (II) are bonded to an oxidic layer, which is an electrode or an insulating layer, via the single bond(s) of the group $A_n$.

2. An alignment film for liquid crystals as claimed in claim 1, wherein the radical $C_y$ is a carbocyclic ring having 12 to 30 ring atoms.

3. An alignment film for liquid crystals as claimed in claim 2, wherein the carbocyclic ring contains 1–4 fused benzene rings thereon.

4. An alignment film for liquid crystals as claimed in claim 1, wherein the radical $C_y$ is selected from the group consisting of:

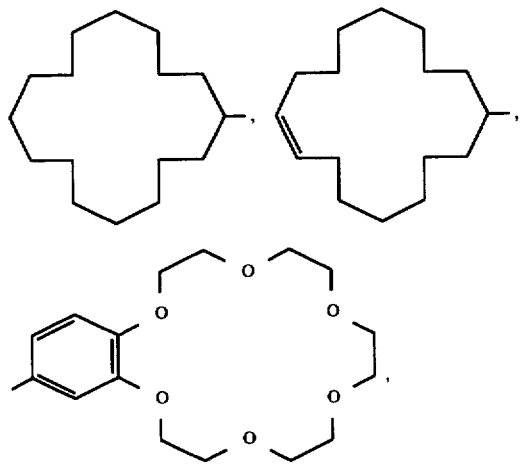

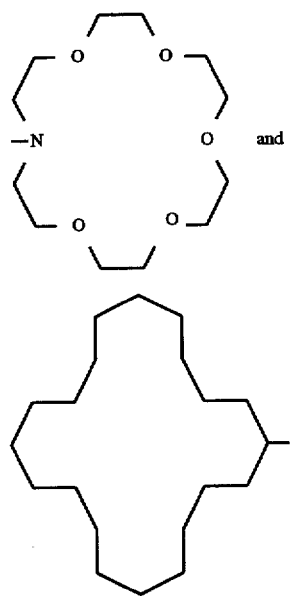

5. An alignment film for liquid crystals as claimed in claim 1, wherein the liquid crystal is ferroelectric.

6. An alignment film for liquid crystals as claimed in claim 1, wherein the oxidic layer is on a substrate.

7. An alignment film for liquid crystals as claimed in claim 1 wherein the oxidic layer is a surface of an oxidic substrate.

8. An alignment film for liquid crystals as claimed in claim 1, wherein the oxidic layer is a surface of an electrode.

9. An electro-optical switching and display device comprising an alignment film as claimed in claim 1.

10. An alignment film for liquid crystals, which comprises chain-form molecules which are bonded to an oxidic substrate via two reactive, silicon-containing groups and which form a loop together with this substrate, wherein the oxidic substrate is an electrode or an insulating layer.

* * * * *